United States Patent
Darrah et al.

(10) Patent No.: US 10,361,001 B2
(45) Date of Patent: Jul. 23, 2019

(54) AUTONOMOUS CRITICAL CARE SYSTEMS AND INTEGRATED COMBAT CASUALTY CARE SYSTEMS

(71) Applicant: Athena GTX, Inc., Des Moines, IA (US)

(72) Inventors: Mark Darrah, Cumming, IA (US); Cesar Gradilla, Des Moines, IA (US); John Elson, San Antonio, TX (US); Ellen Miller, West Des Moines, IA (US)

(73) Assignee: Athena GTX, Inc., Johnston, IA (US)

( * ) Notice: Subject to any disclaimer, the term of this patent is extended or adjusted under 35 U.S.C. 154(b) by 72 days.

(21) Appl. No.: 15/274,618

(22) Filed: Sep. 23, 2016

(65) Prior Publication Data

US 2017/0079733 A1    Mar. 23, 2017

Related U.S. Application Data

(60) Provisional application No. 62/222,617, filed on Sep. 23, 2015.

(51) Int. Cl.
*A61B 50/20* (2016.01)
*A61B 5/08* (2006.01)
(Continued)

(52) U.S. Cl.
CPC .......... *G16H 40/63* (2018.01); *A61B 5/0022* (2013.01); *A61B 5/0205* (2013.01); *A61B 50/31* (2016.02); *A61G 1/00* (2013.01); *A61G 1/048* (2013.01); *A61M 5/168* (2013.01); *A61M 16/0051* (2013.01); *A61M 16/024* (2017.08); *G06F 19/321* (2013.01); *G06F 19/3418* (2013.01); *G06F 19/3481* (2013.01); *A61B 5/742* (2013.01); *A61B 2505/01* (2013.01); *A61M 16/01* (2013.01); *A61M 16/101* (2014.02);
(Continued)

(58) Field of Classification Search
None
See application file for complete search history.

(56) References Cited

U.S. PATENT DOCUMENTS

| | | | | |
|---|---|---|---|---|
| 4,584,989 A | * | 4/1986 | Stith | ........................ A61G 7/00 128/870 |
| 5,494,051 A | * | 2/1996 | Schneider, Sr. | .......... A61G 1/00 128/870 |

(Continued)

*Primary Examiner* — Brian T Gedeon
(74) *Attorney, Agent, or Firm* — Remenick PLLC

(57) ABSTRACT

Systems, devices, and methods for monitoring and treating a patient on route to a medical facility are disclosed. The system comprises a critical care unit; at least one patient monitoring device coupled to the critical care unit, wherein the critical care unit obtains physiological data about the patient from each patient monitoring device; at least one patient treatment device coupled to the critical care unit, wherein the critical care unit provides treatment instructions to each patient treatment device; a two way communications device coupled to the critical care unit; and a remote communications terminal in communication with the two way communications device. The critical care unit preferably sends the physiological data to the remote communications terminal and receives the treatment instructions from the remote communications terminal via the two way communications device.

21 Claims, 3 Drawing Sheets

(51) Int. Cl.

| | | |
|---|---|---|
| *A61M 5/168* | (2006.01) | |
| *G06F 19/00* | (2018.01) | |
| *A61M 16/00* | (2006.01) | |
| *A61G 1/00* | (2006.01) | |
| *A61G 1/048* | (2006.01) | |
| *A61G 1/052* | (2006.01) | |
| *A61B 5/00* | (2006.01) | |
| *A61M 1/00* | (2006.01) | |
| *G16H 40/63* | (2018.01) | |
| *A61B 5/0205* | (2006.01) | |
| *A61B 50/31* | (2016.01) | |
| *A61M 16/01* | (2006.01) | |
| *A61M 16/10* | (2006.01) | |

(52) U.S. Cl.
CPC . *A61M 2016/1025* (2013.01); *A61M 2205/17* (2013.01); *A61M 2205/3553* (2013.01); *A61M 2205/3561* (2013.01); *A61M 2205/3584* (2013.01); *A61M 2205/3592* (2013.01); *A61M 2205/36* (2013.01); *A61M 2205/502* (2013.01); *A61M 2205/8206* (2013.01); *A61M 2209/08* (2013.01); *A61M 2230/00* (2013.01); *A61M 2230/04* (2013.01); *A61M 2230/432* (2013.01)

(56) References Cited

U.S. PATENT DOCUMENTS

| | | | | |
|---|---|---|---|---|
| 5,626,151 | A * | 5/1997 | Linden | A61G 1/00 128/897 |
| 5,755,478 | A * | 5/1998 | Kamiya | A61G 3/001 296/19 |
| 5,918,331 | A * | 7/1999 | Hall | A61G 1/00 296/20 |
| 6,175,977 | B1 * | 1/2001 | Schumacher | A61G 1/04 128/845 |
| 6,493,890 | B2 * | 12/2002 | Smeed | A61G 1/04 108/49 |
| 6,842,922 | B2 * | 1/2005 | Smeed | A61G 1/04 108/49 |
| 6,848,444 | B2 * | 2/2005 | Smith | A61M 16/00 128/204.18 |
| 6,899,103 | B1 * | 5/2005 | Hood | A61G 1/00 128/845 |
| 8,033,281 | B2 * | 10/2011 | Kneale | A61G 1/04 128/845 |
| 9,687,401 | B2 * | 6/2017 | Alford | A63B 71/0619 |
| 9,838,836 | B2 * | 12/2017 | Hayes | A61G 7/018 |
| 9,861,550 | B2 * | 1/2018 | Ribble | G16H 50/30 |
| 2009/0124868 | A1 * | 5/2009 | Barnett | A61N 1/3968 600/301 |

* cited by examiner

AUTONOMOUS CRITICAL CARE SYSTEMS AND INTEGRATED COMBAT CASUALTY CARE SYSTEMS

REFERENCE TO RELATED APPLICATIONS

The present application claims priority to Provisional U.S. Application No. 62/222,617, filed Sep. 23, 2015, entitled "AUTONOMOUS CRITICAL CARE SYSTEMS AND INTEGRATED COMBAT CASUALTY CARE SYSTEMS," and is incorporated herein in its entirety.

RIGHTS IN THE INVENTION

This invention was made with government support under Contract Number N0001414C0347, awarded by the Office Naval Research, and, accordingly, the United States government has certain rights in this invention.

BACKGROUND

1. Field of the Invention

The invention is directed to self-contained medical care platforms. Specifically, the invention is directed to light weight, portable self-contained medical care devices, tools and methods.

2. Background of the Invention

When transporting a patient on a stretcher, such as a NATO ("North Atlantic Treaty Organization") litter, a large metal bracket called a SMEED ("Special Medial Emergency Evacuation Device") is sometimes mounted to the side frame members of the stretcher. The SMEED extends over the patient and serves as a mounting bracket for receiving a plurality of life support devices that function independently of one another. There are several problems associated with the use of the SMEED however. One problem is that the SMEED obstructs access to the patient. Additionally, the SMEED is heavy and cumbersome to use. Loading the SMEED with a variety of different respiratory support and monitoring devices is inefficient from the standpoint of space consumption and weight (the SMEED itself can weigh up to 22 pounds) and does not provide equal optimal access to each of those devices. Accordingly, there is a great need for a portable emergency support device that overcomes the weight, size, positioning, and other portability disadvantages of the SMEED, allows for easy loading of various medical support devices in proximity to a subject during the course of emergency transport.

SUMMARY OF THE INVENTION

The present invention overcomes the problems and disadvantages associated with current strategies and designs and provides new tools and methods of providing portable medical support devices.

One embodiment of the invention is directed to a system for monitoring and treating a patient on route to a medical facility. The system comprise a critical care unit, at least one patient monitoring device coupled to the critical care unit, wherein the critical care unit obtains physiological data about the patient from each patient monitoring device, at least one patient treatment device coupled to the critical care unit, wherein the critical care unit provides treatment instructions to each patient treatment device, a two way communications device coupled to the critical care unit, and a remote communications terminal in communication with the two way communications device. The critical care unit sends the physiological data to the remote communications terminal and receives the treatment instructions from the remote communications terminal via the two way communications device.

Preferably, the critical care unit further comprising a coupling device adapted to attach the system to a patient transport litter. In a preferred embodiment, the coupling device is adjustable to fit different sized liters. Preferably, at least a portion of the critical care unit is adapted to be coupled under the litter. Preferably, the entirety of the critical care unit is adapted to be coupled under the litter. The critical care unit is preferably foldable into a wearable configuration. The critical care unit preferably weighs less than 15 pounds.

In a preferred embodiment, the critical care unit provides at least 80% accessibility to the patient. Preferably, the system comprising redundancies to alleviate equipment failure, to backup the system, and to run multiple similar monitors or therapeutic devices simultaneously. In a preferred embodiment, the critical care unit is adapted to interface with at least one of medical monitors, capnography devices, IV control devices, suction devices, mechanical ventilation devices, concentrated gasses, central computing platforms, and web-based user networks and interfaces. Preferably, the at least one patient treatment device is at least one of a fluid and drug therapy device, an oxygen generating device, a ventilation device, a suction device, and an analgesia/anesthesia device. The system is adapted to preferably monitor and provide treatment to multiple patients simultaneously. The system preferably further comprises at least one visual communications device adapted to provide images of the patient to an offsite medical care giver and provide the patient with images of the offsite medical care giver.

Another embodiment of the invention is directed to a portable critical care unit adapted to monitor and treat a patient on route to a medical facility. The unit comprises at least one patient monitoring device, wherein the critical care unit obtains physiological data about the patient from each patient monitoring device, at least one patient treatment device, wherein the critical care unit provides treatment instructions to each patient treatment device, a two way communications device adapted to send physiological data and receive treatment instructions, and a coupling device adapted to attach the critical care unit to a patient transport litter.

Preferably, the coupling device is adjustable to fit different sized liters. In a preferred embodiment, at least a portion of the critical care unit is adapted to be coupled under the litter. In a preferred embodiment, the entirety of the critical care unit is adapted to be coupled under the litter. Preferably, the critical care unit is foldable into a wearable configuration. The critical care unit preferably weighs less than 15 pounds. Preferably, critical care unit provides at least 80% accessibility to the patient.

The critical care unit preferably further comprises redundancies to alleviate equipment failure, to backup the system, and to run multiple similar monitors or therapeutic devices simultaneously. Preferably, the critical care unit is adapted to interface with at least one of medical monitors, capnography devices, IV control devices, suction devices, mechanical ventilation devices, concentrated gasses, central computing platforms, and web-based user networks and interfaces.

Preferably, the at least one patient treatment device is at least one of a fluid and drug therapy device, an oxygen generating device, a ventilation device, a suction device, and an analgesia/anesthesia device. In a preferred embodiment the critical care unit is adapted to monitor and provide treatment to multiple patients simultaneously. Preferably, the critical care unit further comprises at least one visual communications device adapted to provide images of a patient to an offsite medical care giver and provide the patient with images of the offsite medical care giver.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention It has surprisingly been discovered that a patients chances of survival can be greatly improved with the use of a mobile care system that is adapted to receive data from and control a variety of medical monitoring and treatment devices. The system may be remotely controlled by a medical care giver who has access to the data and is able to send instructions to the mobile care system to control the treatment of the patient. For example, a doctor can access the mobile care system through the internet and begin to provide treatment to the patient while the patient is on route to the hospital.

Figure 1:
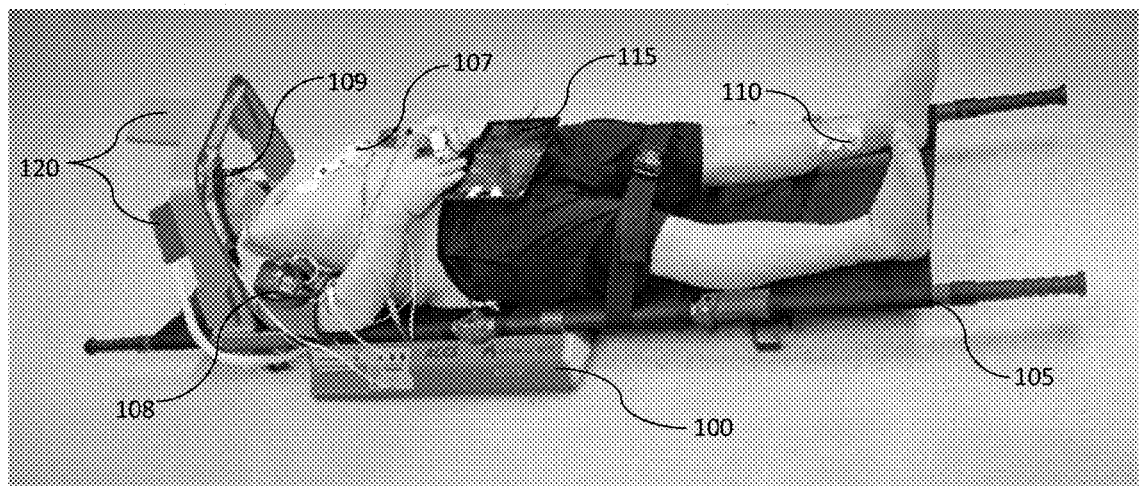
FIG. 1 depicts an embodiment of a system for monitoring and treating a patient.

FIG. 1 depicts an embodiment of an under-litter 105, medical monitoring device 100. Preferably the medical monitoring device 100 is an autonomous critical care system (ACCS). The ACCS system preferably includes computerized advanced technologies for wireless telemedicine and near real-time monitoring, ventilation technologies and sustained oxygen supply/generation, multiple channels of controllable critical care IV/IO ("intravenous/intraosseous") fluids and blood products, TCCC/PHTLS ("Tactical Combat Casualty Care/Pre-Hospital Trauma Life Support") drugs, patient and fluid warming, embedded three dimensions of Decision Support ("DS") as well as provisions for testing and evaluation. Preferably, the ACCS may include integration with total body impedance non-invasive cardiovascular monitoring, wireless 12 lead ECG, stroke volume, cardiac output, total body water, hemoglobin, differential pulse integrity, capnography, and cardiac power including trending of all vital signs simultaneously. Additionally, there may be data integration with ventilation, cardiac pacing, and automatic defibrillation. Preferably, advanced ONR ("Office of Naval Research") MFBS ("Multifunctional Blood Substitute") and dried plasma therapy is adapted for automatic use in the ACCS. Patient cooling for advanced TBI ("Traumatic Brain Injury") or neural injuries is also possible. Control of the system is preferably supplied by miniature dual-redundant integrated custom computer modules, with an embedded remote physician control of patient care via a unique medical GUI ("Graphical User Interface"). Command and control is preferably provided for up to six hours of poly-trauma unmanned care which can be expanded to 72 hours with manned resupply support. The systems can be configured as a standalone single casualty or multi patient system simultaneously in flight in the desired control modes offered. Software preferably automatically recognizes the peripheral devices linked and autonomously configures the display of the data streams to remote care providers as well as attending care providers via tablet and DROID via plug in.

The objective of the ACCS device is to link the casualty to the care provider earlier in the treatment cycle and allowing remote subject matter experts to contribute fully to improved care and better outcomes. Data is preferably controlled and stored for the entire runtime of the transport allowing for subsequent analysis. Remote physicians preferably combine and summarize data feeds, as needed, in order to derive existing and new medical status indices and update and integrate with improved understanding, products and therapies. Advanced predictive and anticipative models are running inside the system based on trauma state, to predict the need for life saving intervention (LSI's) earlier and potential outcomes based on patient vitals and ETA.

Preferably, the ACCS 100 is couple-able to the underside of a liter 105 and provides at least 80% accessibility to the patient. Preferably, the ACCS 100 has adjustable couplings adapted to fit different sized liters. The ACCS is preferably less than 30 pounds and more preferably less than 15 pounds. Preferably, the ACCS is adapted to run on rechargeable batteries for up to 4, up to 6, or preferably up to 8 hours without recharging. Additionally, the ACCS may be adapted to plug into conventional wall outlets. Preferably, the ACCS is adapted to withstand moisture and dust. For example, the ACCS may be water and wind proof, hermetically sealed, or otherwise impervious to the elements.

As shown in FIG. 1, various medical monitoring and therapeutic devices (106-110) are preferably simultaneously controlled by the ACCS 100. Preferably ACCS 100 has redundancies to allow for equipment failure, backup, and running multiple similar monitors or therapeutic devices (e.g. providing multiple IV lines simultaneously). ACCS 100 may be in data communication with an external input device (for example tablet 115, or a smartphone). The external input device may allow an onsite care giver to input information about procedures or medications already given to the patient. Preferably, the ACCS 100 has one or more interface points, unified controls and integrated displays.

Figure 2:
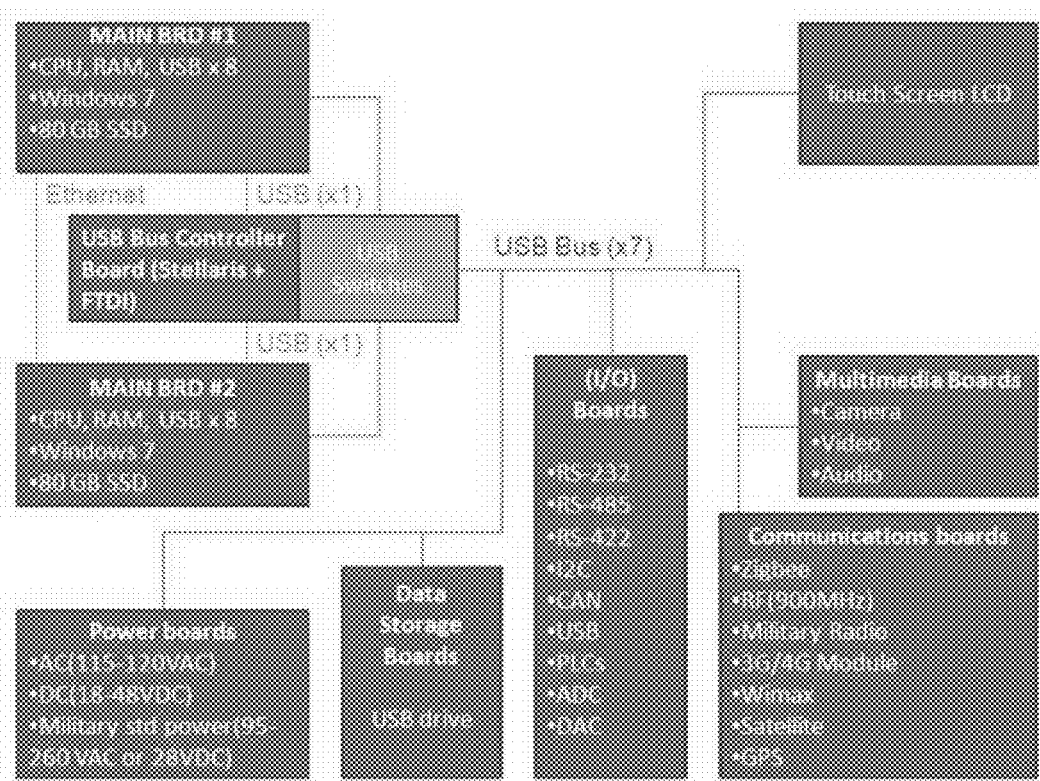
FIG. 2 depicts a schematic of an embodiment of the components of the system in FIG. 1.
Figure 3:
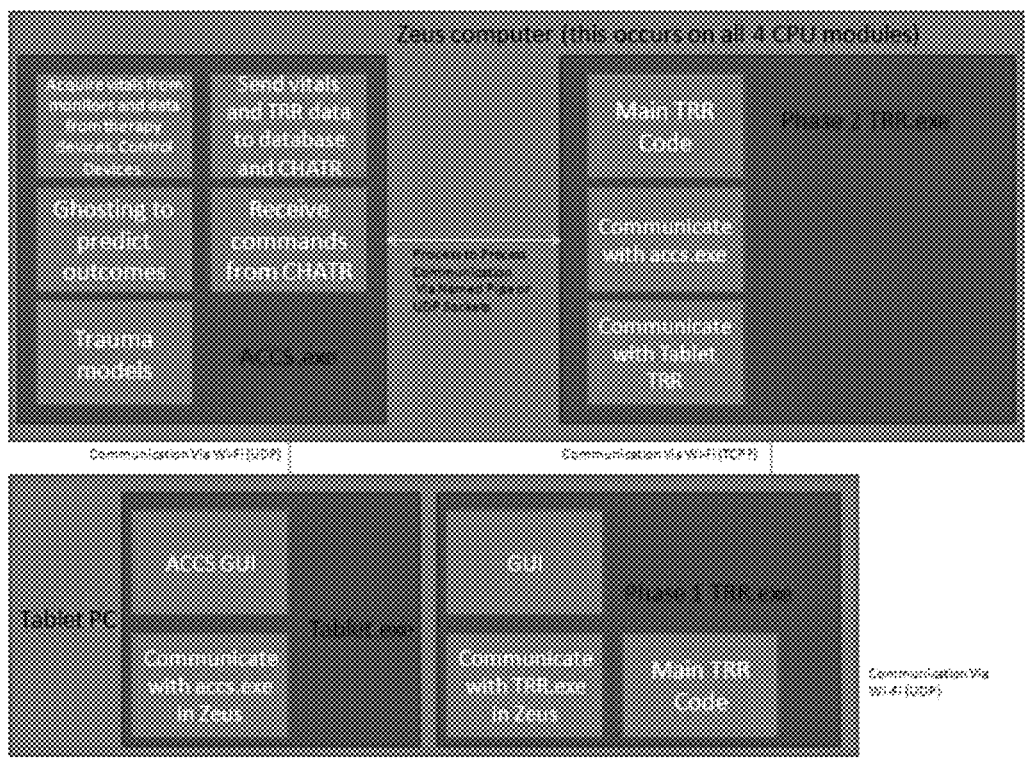
FIG. 3 depicts a schematic of an embodiment of the software used in the system in FIG. 1.

FIG. 2 depicts a schematic of an embodiment of internal computer system of the ACCS, while FIG. 3 depicts a schematic of an embodiment of associated software. Preferably, the ACCS system communicates with multiple wireless and wired hardware devices. Such devices may include, but are not limited to medical monitors (e.g. a defibrillator, or an ECG), capnography devices, IV control devices, suction devices, mechanical ventilation devices, concentrated gasses, central computing platforms, and web-based user networks and interfaces. Preferably, the main computer system comprises a CPU ("Computer Processing Unit"), memory (e.g. RAM and/or Flash), wireless (e.g. Wi-Fi and/or Bluetooth) and wired communication protocols. Preferably, the main computer system controls subservient systems and all systems share data to allow duplicate control with minimal delay.

Preferably, main processor boards will communicate with ASBs ("Analog Sensor Boards") or SCBs ("Sensor and Control Boards") via SPI ("Serial Peripheral Interface") that is not susceptible to lost bits, noise, and missing slave devices and will communicate via Ethernet allowing dual redundancy in case of a failure. The design preferably has at least two CPU boards in a master/slave design. Errors, thread and board status will preferably be logged and available to transmit. Preferably, each USB port on the communications board will be separate and will not affect other ports if it fails. Data is preferably stored using a proprietary file format which is not prone to errors during power loss. The system may have multiple threads of execution running different algorithms in parallel reporting to a master thread. The system preferably allows complex DS to be engaged and distributed DS for different patient responses. The system preferably balances redundancy, failure modes, reliability and maintainability.

Preferably, the system has unlimited and redundant monitor capability. For example, in FIG. 1 there are three screens 120 positioned on a support around the patient that allows the patient to interact with an off-site medical care provider. For example, the off-site medical care provider may be able to view the patient to assess the patient's condition through cameras. The baseline consists of display boards with HDMI and VGA will connect to a remote monitor. The system is preferably populated with boards that are hot swappable or changed out on sensor and PC modules. Data is preferably stored using a common/standard file format such as FAT or FAT32 with multiple redundant storage devices. Preferably, power boards enable the device to be powered by various power sources available to military personnel. GPS board preferably runs diagnostic location and determines positioning. The system preferably has multiple threads of execution running different algorithms in parallel reporting to a master thread. The system preferably allows complex DS to be engaged and distributed DS for different patient responses. Preferably, the system balances redundancy, failure modes, reliability and maintainability. Individual sensor and control boards (SCBs) are integrated into the system and operate independently. Complex patient information is asynchronously collected and processed by each of these SCBs. The main processing board communicates with the SCBs using a combination of high-speed SPI and UART ("Universal Asynchronous Receiver/Transmitter"). Various framing and checksum protocols are employed to guarantee data integrity during communications. The main processing board and SCBs maintain a "master-slave" relationship, whereby the SCBs operate under the direction of the main processing board. However, where appropriate, the SCBs can detect if they are no longer being properly controlled and respond by disengaging or maintaining state. In another embodiment, the system is preferably designed with highly efficient ASB communication via SPI. The device is preferably the SPI master and any ASBs are the SPI slaves. Each ASB preferably has algorithms built-in to allow safe operation in case of a communications failures. The ASB may be able to automatically determine that it is no longer being properly controlled by the application.

The data from any connected system components is preferably captured, stored, and displayed (both patient and system information) with preferably at least 99% accuracy.

Preferably, the system provides for closed-loop-control maintenance of body temperature at +/−1 degree F. Preferably external physiological and hemodynamic monitoring system components: monitor, record and display heart rate (derived from ECG); have 3-12 lead ECG monitoring capability; have arrhythmia detection and alarm capability; capture and record respiratory rate, pulse-oximetry, and non-invasive cardiac output, total peripheral resistance, stroke volume; have multiple channels for intravascular catheters; have clinical parameters and waveforms that are visualized with at least 99% accuracy during movement; and have wireless patient monitoring capability to include SPO2. Preferably fluid and drug therapy external components: are decision-assist and closed-loop control capable; record (date and time stamp) patient measurements and interventions, and cumulative total fluid received (infused and net volumes); have decision-assist and closed-loop control algorithms control rate and volume of multiple fluids (crystalloids, colloids, blood/blood products); have fluid warming to approximately 40° F. capability; be rapid fluid infuser capable (e.g. 6 L/hr) with free-flow protection and vented bubble detection/removal; have industry standard alarms (audio and visual), including low battery alarm; provide a library of medications of commonly used drugs to treat trauma patients (e.g. epinephrine, phenylephrine, dopamine, vasopressin, paralytics, etc), and a system to allow drug calculations.

Preferably, the ACCS includes an oxygen generating system that: provides at least 6 L/min of 93% United States Pharmacopeia (USP) oxygen (+/−) 5%; provides inspired oxygen (FiO2) range of 21% to 100%; controls low flow oxygen source to maintain stable FiO2. Preferably, the ACCS includes a ventilation system that: has a filter system for ventilation that is 100% CBRN effective; has decision-assist and closed-loop algorithms for delivery of FiO2 (21-100%) and positive end-expiratory pressure (PEEP) (0-25+/−1 cm H2O); has a flow capable ventilator (100 L/min at 40 cm H2O); controls low flow oxygen source to maintain stable FiO2+/−5% and an alarm; has pressure- and volume-controlled ventilation modes for pediatric and adults; accepts oxygen input pressure of about 35-70 psi; displays and monitors inspired oxygen concentration (FiO2) and end tidal CO2; provides humidified oxygen (100% saturation); allows administration of aerosolized medications; has programmable standard of care alarms, including low pressure, high pressure, apnea, low source gas pressure, power supply low, low minute ventilation, high respiratory rate; has decision-assist algorithms for each alarm condition; automatically restarts after unexpected loss of power with user approved settings before reinitiating; creates exportable records of ventilator performance; displays operational time remaining for battery life; and has time stamp, capture and playback capability for waveforms and significant events.

Preferably there is a suction system that: is capable of suctioning with variable digital control and intermittent and constant suction capable of high/low endotracheal tube, gastric, and chest tube; has controlled suction capability (10-300 mm Hg); and has pop-off valves. Preferably, there is an Analgesia/Anesthesia system that has standard of care and total intravenous anesthesia (TIVA) capability and is BIS monitoring capable. Preferably, the external components have manuals, simulation and training software to familiarize medical personnel with operation and maintenance of each system.

The system preferably has wireless capability that: provides for physician monitoring of patient status and a system override capability from a remote medical treatment facility and has wireless patient monitoring capability. Preferably, the system is accessible over the internet from remote locations. For example, the system may us cellular networks, satellite networks, or Wi-Fi networks to communicate with the internet. Preferably, the system has manually adjustable audible and visual alarms over an intensity range of 0-100% with 99% effectiveness and accuracy while operating. The system preferably uses industry standard data storage and data transfer technology to capture, store, and display both patient and system information at a minimum of 72 hours. The system preferably has an open architecture to log and store patient clinical parameters and waveforms at a minimum of 72 hours, provide for data transfer between the device and a remote medical treatment facility, and has simulation and training software to familiarize medical personnel with operation and maintenance of device.

Figure 4:
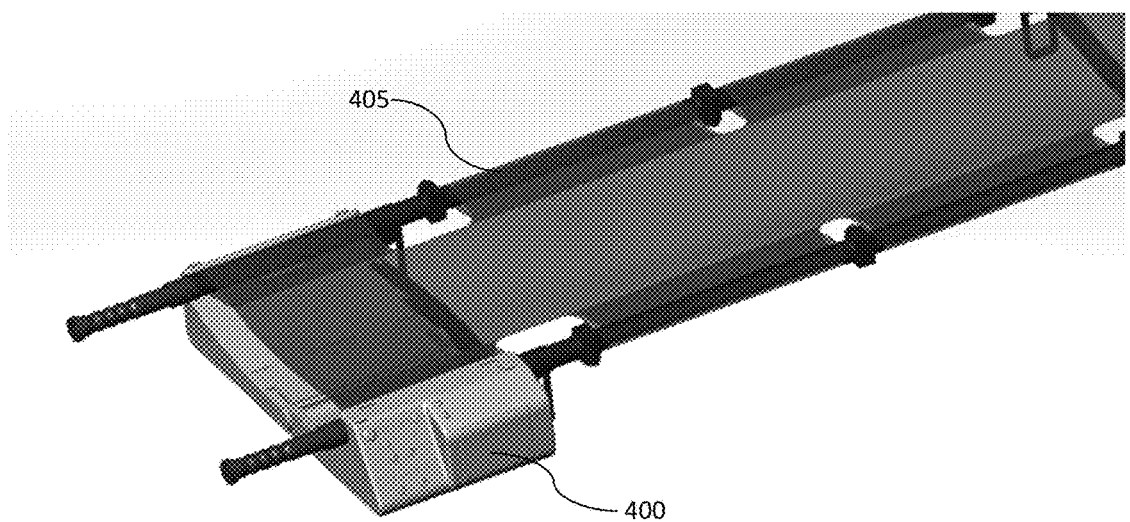
FIGS. 4 and 5 depict another embodiment of a system for monitoring and treating a patient in two configurations.
Figure 5:
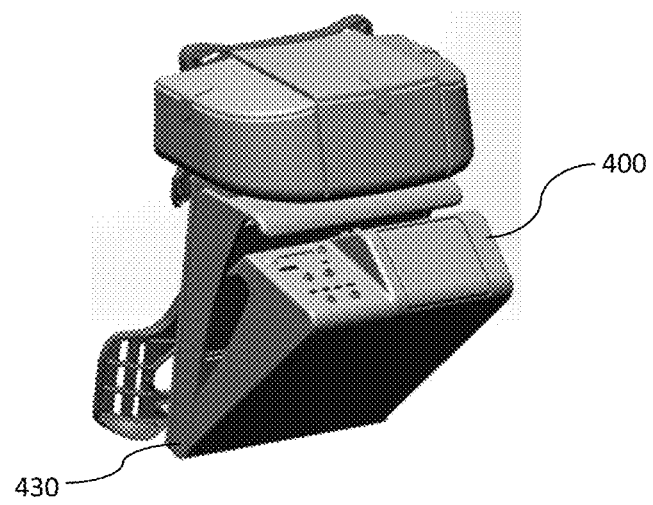

FIG. 4 depicts an embodiment of an Integrated Combat Casualty Care System ("ICCCS") 400 coupled to a litter 405. FIG. 5 depicts the ICCCS 400 folded into a wearable configuration (i.e. the backpack in FIG. 5). Preferably, the ICCCS is similar to the ACCS, however the ICCCS is lighter than the ACCS and has a hinge 430 that allows the ICCCS to fold into a wearable configuration. The ICCCS system is preferably reduced in weight and bulk from the ACCS to a 10-12 pound backpack option. ICCCS is preferably a modular, highly mobile system consisting of two processing modules, two power modules, and one peripheral module. The two processing modules are preferably configured as a Dual Modular Redundant (DMR) system in a master/slave configuration. The peripheral module preferably consists of several independent channels with interface to a SAVe II ventilator, two or more channels of fluids via PSID which are user-controlled, with controllable fluid warming on each channel, two or four independent channels of controllable suction with fluid storage and state of the art monitoring. ICCCS preferably provides single or multi-patient control access via DROID or tablet with electronic TCCC. The device is preferably fielded with abilities to link wirelessly or wired and can communicate with wireless battlefield communications systems when cleared and available. The ICCCS device preferably integrates oxygen generation but can alternatively integrate with other oxygen delivery mechanisms.

Figure 6:
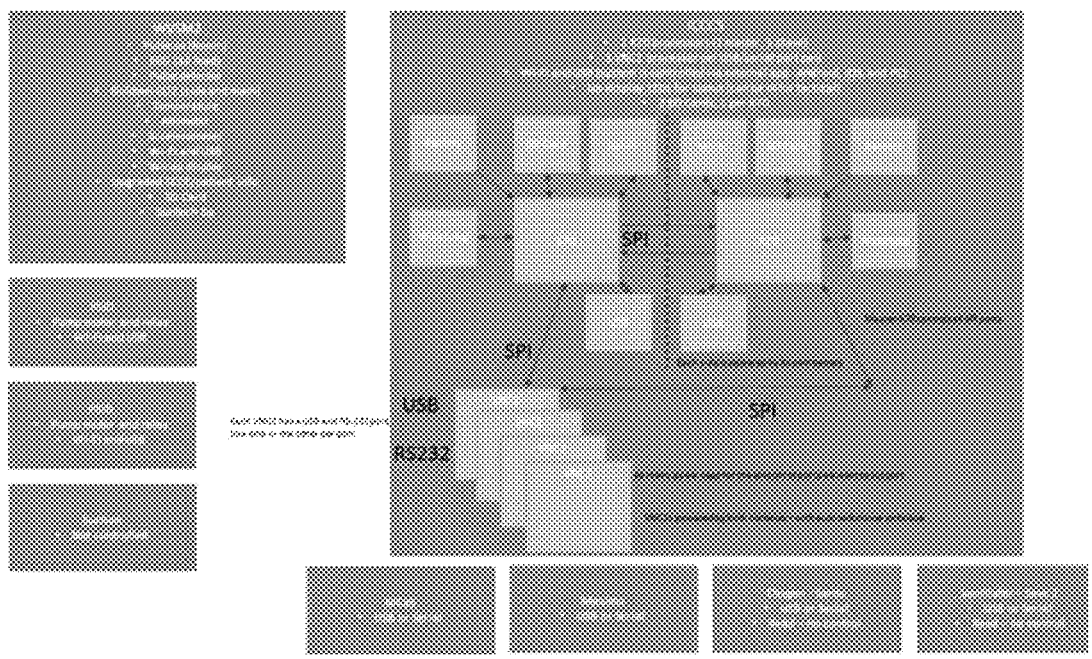
FIG. 6 depicts a schematic of an embodiment of the components of the system in FIGS. 4 and 5.

The ICCCS is preferably a modular, wirelessly enabled, complete critical care solution for use with manned and unmanned medical transport and evacuation operations. It exercises the highest level of automation and decision assistance possible for such systems. The core functionality for the ICCCS is preferably provided with multiple connected hardware devices, software and user-interfaces. FIG. 6 depicts an embodiment of the ICCCS system layout.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A system for monitoring and treating a patient en route to a medical facility, comprising:
    a critical care unit, wherein the critical care unit has a single hinge adapted to fold the critical care unit from a backpack configuration, transportable separately from a patient transport litter, into a configuration adapted to be coupled underneath the patient transport litter;
    at least one patient monitoring device coupled to the critical care unit, wherein the critical care unit obtains physiological data about the patient from the at least one patient monitoring device and transmits instructions to the patient monitoring device;
    at least one patient treatment device coupled to the critical care unit, wherein the critical care unit provides treatment instructions to the at least one patient treatment device and received feedback from the patient treatment device;
    at least one peripheral device linkage, wherein the critical care unit is adapted to automatically recognize and configure each linked peripheral device;
    a two way communications device coupled to the critical care unit; and
    a remote communications terminal in communication with the two way communications device;
    wherein the critical care unit sends the physiological data to the remote communications terminal and receives the treatment instructions from the remote communications terminal via the two way communications device.

2. The system of claim 1, the critical care unit further comprising a coupling device adapted to attach the system to the patient transport litter.

3. The system of claim 2, wherein the coupling device is adjustable to fit different sized litters.

4. The system of claim 1, wherein the entirety of the critical care unit is adapted to be coupled under the litter.

5. The system of claim 1, wherein the critical care unit weighs less than 15 pounds.

6. The system of claim 1, wherein the critical care unit provides at least 80% accessibility to the patient.

7. The system of claim 1, further comprising redundancies to alleviate equipment failure, to backup the system, and to run multiple similar monitors or therapeutic devices simultaneously.

8. The system of claim 1, wherein the critical care unit is adapted to interface with at least one of medical monitors, capnography devices, IV control devices, suction devices, mechanical ventilation devices, concentrated gasses, central computing platforms, and web-based user networks and interfaces.

9. The system of claim 1, wherein the at least one patient treatment device is at least one of a fluid and drug therapy device, an oxygen generating device, a ventilation device, a suction device, and an analgesia/anesthesia device.

10. The system of claim 1, wherein the system is adapted to monitor and provide treatment to multiple patients simultaneously.

11. The system of claim 1, further comprising at least one visual communications device adapted to provide images of the patient to an offsite medical care giver and provide the patient with images of the offsite medical care giver.

12. A portable critical care unit adapted to monitor and treat a patient en route to a medical facility, comprising:
    at least one patient monitoring device, wherein the critical care unit obtains physiological data about the patient from the at least one patient monitoring device and transmits instructions to the patient monitoring device;
    at least one patient treatment device, wherein the critical care unit provides treatment instructions to the at least one patient treatment device and received feedback from the patient treatment device;

at least one peripheral device linkage, wherein the critical care unit is adapted to automatically recognize and configure each linked peripheral device;

a two way communications device adapted to send physiological data and receive treatment instructions; and a coupling device adapted to attach the critical care unit to a patient transport litter, wherein the critical care unit has a single hinge adapted to fold the critical care unit from a backpack configuration, transportable separately from a patient transport litter, into a configuration adapted to be coupled underneath the patient transport litter.

13. The critical care unit of claim 12, wherein the coupling device is adjustable to fit different sized litters.

14. The critical care unit of claim 12, wherein the entirety of the critical care unit is adapted to be coupled under the litter.

15. The critical care unit of claim 12, wherein the critical care unit weighs less than 15 pounds.

16. The critical care unit of claim 12, wherein critical care unit provides at least 80% accessibility to the patient.

17. The critical care unit of claim 12, further comprising redundancies to alleviate equipment failure, to backup the system, and to run multiple similar monitors or therapeutic devices simultaneously.

18. The critical care unit of claim 12, wherein the critical care unit is adapted to interface with at least one of medical monitors, capnography devices, IV control devices, suction devices, mechanical ventilation devices, concentrated gasses, central computing platforms, and web-based user networks and interfaces.

19. The critical care unit of claim 12, wherein the at least one patient treatment device is at least one of a fluid and drug therapy device, an oxygen generating device, a ventilation device, a suction device, and an analgesia/anesthesia device.

20. The critical care unit of claim 12, wherein the critical care unit is adapted to monitor and provide treatment to multiple patients simultaneously.

21. The critical care unit of claim 12, further comprising at least one visual communications device adapted to provide images of a patient to an offsite medical care giver and provide the patient with images of the offsite medical care giver.

* * * * *